(12) United States Patent
Bose et al.

(10) Patent No.: US 11,972,575 B2
(45) Date of Patent: Apr. 30, 2024

(54) SYSTEMS AND METHODS FOR GENERATING AUGMENTED SEGMENTED IMAGE SET

(71) Applicant: UIH AMERICA, INC., Houston, TX (US)

(72) Inventors: Supratik Bose, Walnut Creek, CA (US); Jonathan Maltz, Walnut Creek, CA (US)

(73) Assignee: UIH AMERICA, INC., Houston, TX (US)

(*) Notice: Subject to any disclaimer, the term of this patent is extended or adjusted under 35 U.S.C. 154(b) by 950 days.

(21) Appl. No.: 16/892,311

(22) Filed: Jun. 4, 2020

(65) Prior Publication Data

US 2020/0302613 A1 Sep. 24, 2020

Related U.S. Application Data

(63) Continuation of application No. 16/004,387, filed on Jun. 9, 2018, now Pat. No. 10,685,445.

(51) Int. Cl.
*G06T 7/168* (2017.01)
*A61N 5/10* (2006.01)
*G06T 7/11* (2017.01)

(52) U.S. Cl.
CPC .......... *G06T 7/168* (2017.01); *A61N 5/1039* (2013.01); *G06T 7/11* (2017.01); *G06T 2207/10081* (2013.01); *G06T 2207/20081* (2013.01)

(58) Field of Classification Search
CPC ......... G06T 7/168; G06T 7/11; G06T 7/0014; G06T 7/12; G06T 7/149; G06T 7/33;
(Continued)

(56) References Cited

U.S. PATENT DOCUMENTS 7,225,011 B2 * 5/2007 Mielekamp ............ G16H 50/50
600/407
2016/0063720 A1 3/2016 Han et al.
(Continued)

FOREIGN PATENT DOCUMENTS

CN 107123095 A 9/2017

OTHER PUBLICATIONS

G Sharp et al., Vision 20/20: Perspectives on automated image segmentation for radiotherapy, Med. Phys. 41 (5), 2014, 13 pages.
(Continued)

*Primary Examiner* — Mekonen T Bekele
(74) *Attorney, Agent, or Firm* — METIS IP LLC

(57) ABSTRACT

A system and method for generating augmented segmented image set obtain are provided. The method may include: obtaining a first image including a first anatomical structure of a first object; determining first feature data of the first anatomical structure; determining one or more first transformations related to the first anatomical structure, wherein a first transformation includes a transformation type and one or more transformation parameters related to the transformation type; applying the one or more first transformations to the first feature data of the first anatomical structure to generate second feature data of the first anatomical structure; and generating a second image based on the second feature data of the first anatomical structure.

20 Claims, 11 Drawing Sheets

(58) Field of Classification Search
CPC ......... G06T 11/003; G06T 2207/10081; G06T 2207/20081; A61N 5/1039; G06N 3/045
See application file for complete search history.

(56) References Cited

U.S. PATENT DOCUMENTS

| | | | |
|---|---|---|---|
| 2016/0166141 A1* | 6/2016 | Kanagasingam | A61B 3/12 351/246 |
| 2016/0166333 A1 | 6/2016 | Wang et al. | |
| 2018/0035981 A1* | 2/2018 | Song | A61B 8/5207 |
| 2018/0225993 A1* | 8/2018 | Buras | A61B 8/06 |
| 2018/0360408 A1 | 12/2018 | Quan | |
| 2019/0099619 A1 | 4/2019 | Maltz | |
| 2019/0175942 A1 | 6/2019 | Stahl et al. | |
| 2019/0209864 A1 | 7/2019 | Stahl et al. | |
| 2019/0209868 A1 | 7/2019 | Stahl et al. | |
| 2020/0030038 A1 | 1/2020 | Wang et al. | |

OTHER PUBLICATIONS

T. Heimann et al., Statistical shape models for 3D medical image segmentation: A review, Medical Image Analysis, 13: 543-563, 2009.
Chen-Rui Chou et al., Real-time 2D/3D Deformable Registration Using Metric Learning, Springer-Verlag, 2013, 10 pages.
Liya Zhao et al., Deep Adaptive Log-Demons: Diffeomorphic Image Registration with Very Large Deformations, Computational and Mathematical Methods in Medicine, 2015, 16 pages.
M. R. Avendi et al., A Combined Deep-Learning and Deformable-Model Approach to Fully Automatic Segmentation off the Left Ventricle in Cardiac MRI, Medical Image Analysis, 2016, 34 pages.
G. Wu et al., Unsupervised Deep Feature Learning for Deformable Registration of MR Brain Images, Med Image Comput Comput Assist Interv, 16(2): 649-656, 2013.
Adriano Pinto et al., Brain Tumor Segmentation Using Convolutional Neural Networks in MRI Images, IEEE Transactions on Medical Imaging, 35(5): 1240-1251, 2016.
Fausto Milletari et al., V-Net: Fully Convolutional Neural Networks for Volumetric Medical Image Segmentation, 3D Vision (3DV), 2016 Fourth International Conference on, 565-571, 2016.
Olaf Ronneberger et al., U-Net: Convolutional Networks for Biomedical Image Segmentation, Medical Image Computing and Computer-Assisted Intervention (MICCAI), Springer, LNCS, 9351: 234-241, 2015.
T. F. Cootes et al., Data Driven Refinement of Active Shape Model Search, British Machine Vision Conference, BMVA Press, 1996, 10 pages.
K. Antila et al., Artficial Enlargement of a Training Set for Statistical Shape Models: Application to Cardiac Images, Functional Imaging and Modeling of the Heart, LNCS 3504: 92-101, 2005.
Nan Hu et al., A method for generating large datasets of organ geometries for radiotherapy treatment planning studies, Radiol Oncol 48(4): 408-415, 2014.
Z. Henry Yu et al., Learning anatomy changes from patient populations to create artificial CT images for voxel-level validation of deformable image registration, Journal of Applied Clinical Medical Physics, 17(1): 246-258, 2016.
K. Suzuki et al., Machine Learning in Medical Imaging, Second International workshop MLMI 2011, Springer Verlag, 1-129, 2009.
K. Suzuki et al., Machine Learning in Medical Imaging, Second International workshop MLMI 2011, Springer Verlag, 130-253, 2009.
K. Suzuki et al., Machine Learning in Medical Imaging, Second International workshop MLMI 2011, Springer Verlag, 253-383, 2009.

* cited by examiner

SYSTEMS AND METHODS FOR GENERATING AUGMENTED SEGMENTED IMAGE SET

CROSS-REFERENCE TO RELATED APPLICATIONS

This application is a continuation of U.S. patent application Ser. No. 16/004,387, filed on Jun. 9, 2018, the entire contents of which are hereby incorporated by reference.

TECHNICAL FIELD

The present disclosure generally relates to systems and methods for generating augmented segmented image set, and more particularly, to systems and methods for generating the augmented segmented image set by transforming historical segmented image data.

BACKGROUND

The radiotherapy treatment of a cancer patient may commence typically couple of weeks after a pre-treatment imaging procedure. The pre-treatment imaging procedure simulates a treatment scene where the patient is transported into a specific position inside a gantry of a radiation device. Further, one or more images of the patient are obtained for the doctors or radiologists to determine an original treatment plan. However, the anatomy of the patient may change after the pre-treatment imaging procedure or during the treatment procedure. Based on the amount of change in the anatomy, the original treatment plan may need to be modified in order to reduce the toxicity and improve targeting of the tumor and the overall outcome of the treatment. One of the fundamental tasks during a replanning phase is segmenting and contouring of different targets and organs at risk. Many automated techniques have been developed to provide an initial approximation of the targets and organs at risk as well as to automate the contouring task to a large extent. However, the performance of the automated contouring techniques relies on the availability and the amount of pre-labeled and segmented image data. As the labeled segmented image data is often not available in a large scale, there is a need to generate the labeled segmented data in large scale to improve the performance of automated contouring for the radiotherapy replanning.

SUMMARY

In a first aspect of the present disclosure, a system for generating training data is provided. The system may include at least one processor and instructions. When the at least one processor executes the instructions, the at least one processor may be directed to perform one or more of the following operations. A first image including a first anatomical structure of a first object may be obtained. First feature data of the first anatomical structure may be determined. One or more first transformations related to the first anatomical structure under one or more associated constraints may be determined. A first transformation may include a transformation type and one or more transformation parameters related to the transformation type, and the transformation type may include at least one of a displacement of an anatomical structure, a rotation of the anatomical structure, a deformation of the anatomical structure, an appearance of an extra structure, and a disappearance of partial of the anatomical structure. The one or more first transformations may be applied to the first feature data of the first anatomical structure to generate second feature data of the first anatomical structure. A second image may be generated based on the second feature data of the first anatomical structure.

In some embodiments, the at least one processor may be further directed to perform one or more of the following operations. A transformation sequence related to the one or more first transformations may be determined. The second image may be generated based on the transformation sequence.

In some embodiments, the first feature data or the second feature data may include pixel values and pixel locations of a plurality of first pixels representing a contour of the first anatomical structure, or pixel values and pixel locations of a plurality of second pixels representing an inner area encompassed by the contour of the first anatomical structure.

In some embodiments, to apply the one or more first transformations to the first feature data to generate second feature data, the at least one processor may be further directed to perform one or more of the following operations. A reference frame may be generated by determining one or more fixed points in the first image. The second feature data of the first anatomical structure may be determined based on the reference frame and the one or more transformation parameters.

In some embodiments, to determine the second feature data of the first anatomical structure based on the reference frame and the one or more transformation parameters, the at least one processor may be further directed to perform one or more of the following operations. A center point of the first anatomical structure may be determined. An original position of the first anatomical structure may be determined based on the center point of the first anatomical structure and a reference frame. The second feature data of the first anatomical structure may be determined based on the original position of the first anatomical structure and the one or more transformation parameters.

In some embodiments, the transformation type may include a displacement of an anatomical structure. To apply the one or more transformations to the first feature data, the processor is further configured to perform one or more of the following operations. A displacement vector may be determined based on the one or more transformation parameters. The second feature data may be determined based on the displacement vector and the first feature data.

In some embodiments, the first image further may include a second anatomical structure of the first object, and the processor is further configured to perform one or more of the following operations. A priority order between the first anatomical structure and the second anatomical structure may be determined. The second image may be generated based on the priority order between the first anatomical structure and the second anatomical structure.

In some embodiments, to determine the first transformation of the first anatomical structure, the processor is further configured to perform one or more of the following operations. The one or more transformation parameters related to the transformation type may be determined based on one or more parameter constraints.

In some embodiments, the transformation type may further include an adjustment of a contrast noise ratio or a signal noise ratio.

In some embodiments, the first image may be a planning image with segmented information used in radiation therapy. In some embodiments, the the planning image may be a CT image.

In some embodiments, the processor is further configured to perform one or more of the following operations. A training image set may be generated based on one or more second images. An initial model may be obtained. A trained model may be generated based on the training image set and the initial model.

In some embodiments, the processor is further configured to perform one or more of the following operations. A treatment image containing the first anatomical structure may be obtained. A plurality of pixels with respect to the first anatomical structure may be identified based on the trained model and the treatment image.

In a second aspect of the present disclosure, a system for generating training data is provided. The system may include at least one processor and instructions. When the at least one processor executes the instructions, the at least one processor may be directed to perform one or more of the following operations. A first image of an object associated with a treatment plan may be obtained. The first image may include a first anatomical structure of a first object from a treatment planning phase. First feature data of the first anatomical structure may be determined. One or more first transformations related to the first anatomical structure under one or more associated constraints may be determined. A first transformation may include a transformation type and one or more transformation parameters related to the transformation type, and the transformation type may include at least one of a displacement of an anatomical structure, a rotation of the anatomical structure, a deformation of the anatomical structure, an appearance of an extra structure, and a disappearance of partial of the anatomical structure. The one or more first transformations may be applied to the first feature data of the first anatomical structure to generate second feature data of the first anatomical structure. One or more second images may be generated based on the second feature data of the first anatomical structure. A trained model may be generated based on an initial model and a training image set including one or more second images. A treatment image of the object before or during or after radiotherapy but after the treatment planning phase may be obtained. An image with segmented information may be generated based on the trained model and the treatment image.

In some embodiments, the processor is further configured to perform one or more of the following operations. The treatment plan may be modified based on the image with segment information.

In some embodiments, the first image and the treatment image may be obtained from different modalities.

In some embodiments, the first image and the treatment image may be obtained from different dose levels or different signal noise ratio levels.

In a third aspect of the present disclosure, a method for generating training data is provided. The method may include one or more of following operations. A first image including a first anatomical structure of a first object may be obtained. First feature data of the first anatomical structure may be determined. One or more first transformations related to the first anatomical structure under one or more associated constraints may be determined. A first transformation may include a transformation type and one or more transformation parameters related to the transformation type, and the transformation type may include at least one of a displacement of an anatomical structure, a rotation of the anatomical structure, a deformation of the anatomical structure, an appearance of an extra structure, and a disappearance of partial of the anatomical structure. The one or more first transformations may be applied to the first feature data of the first anatomical structure to generate second feature data of the first anatomical structure. A second image may be generated based on the second feature data of the first anatomical structure.

In a fourth aspect of the present disclosure, a method for generating training data is provided. The method may include one or more of following operations. A planning image including a first anatomical structure of a first object may be obtained. First feature data of the first anatomical structure may be determined. One or more first transformations related to the first anatomical structure under one or more associated constraints may be determined. A first transformation may include a transformation type and one or more transformation parameters related to the transformation type, and the transformation type may include at least one of a displacement of an anatomical structure, a rotation of the anatomical structure, a deformation of the anatomical structure, an appearance of an extra structure, and a disappearance of partial of the anatomical structure. The one or more first transformations may be applied to the first feature data of the first anatomical structure to generate second feature data of the first anatomical structure. An artificial image may be generated based on the second feature data of the first anatomical structure, the artificial image being used as the training data.

In a fifth aspect of the present disclosure, a non-transitory computer readable medium is provided. The non-transitory computer readable medium may include executable instructions. When at least one processor executes the instructions, the at least one processor may effectuate a method including one or more of the following operations. A first image including a first anatomical structure of a first object may be obtained. First feature data of the first anatomical structure may be determined. One or more first transformations related to the first anatomical structure under one or more associated constraints may be determined. A first transformation may include a transformation type and one or more transformation parameters related to the transformation type, and the transformation type may include at least one of a displacement of an anatomical structure, a rotation of the anatomical structure, a deformation of the anatomical structure, an appearance of an extra structure, and a disappearance of partial of the anatomical structure. The one or more first transformations may be applied to the first feature data of the first anatomical structure to generate second feature data of the first anatomical structure. A second image may be generated based on the second feature data of the first anatomical structure.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

Figure 2:
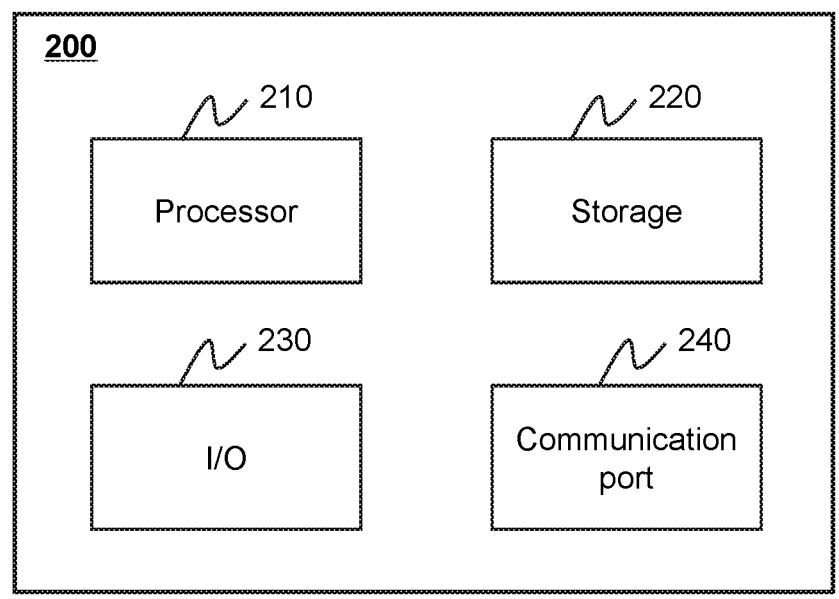
FIG. 2 is a schematic diagram illustrating exemplary hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., the processor 210 as illustrated in FIG. 2) may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for generating augmented segmented image set. The method may include obtaining historical segmented image data. The method may also include generating augmented segmented image set by transforming the historical segmented image data based on one or more transformations. The method may also include segmenting an image of an organ based on a segmentation model trained by the historical segmented image data and the augmented segmented image set. For persons having ordinary skills in the art, a certain amount of variations, changes, and/or modifications may be deducted under the guidance of the present disclosure. Those variations, changes, and/or modifications do not depart from the scope of the present disclosure.

Figure 1A:
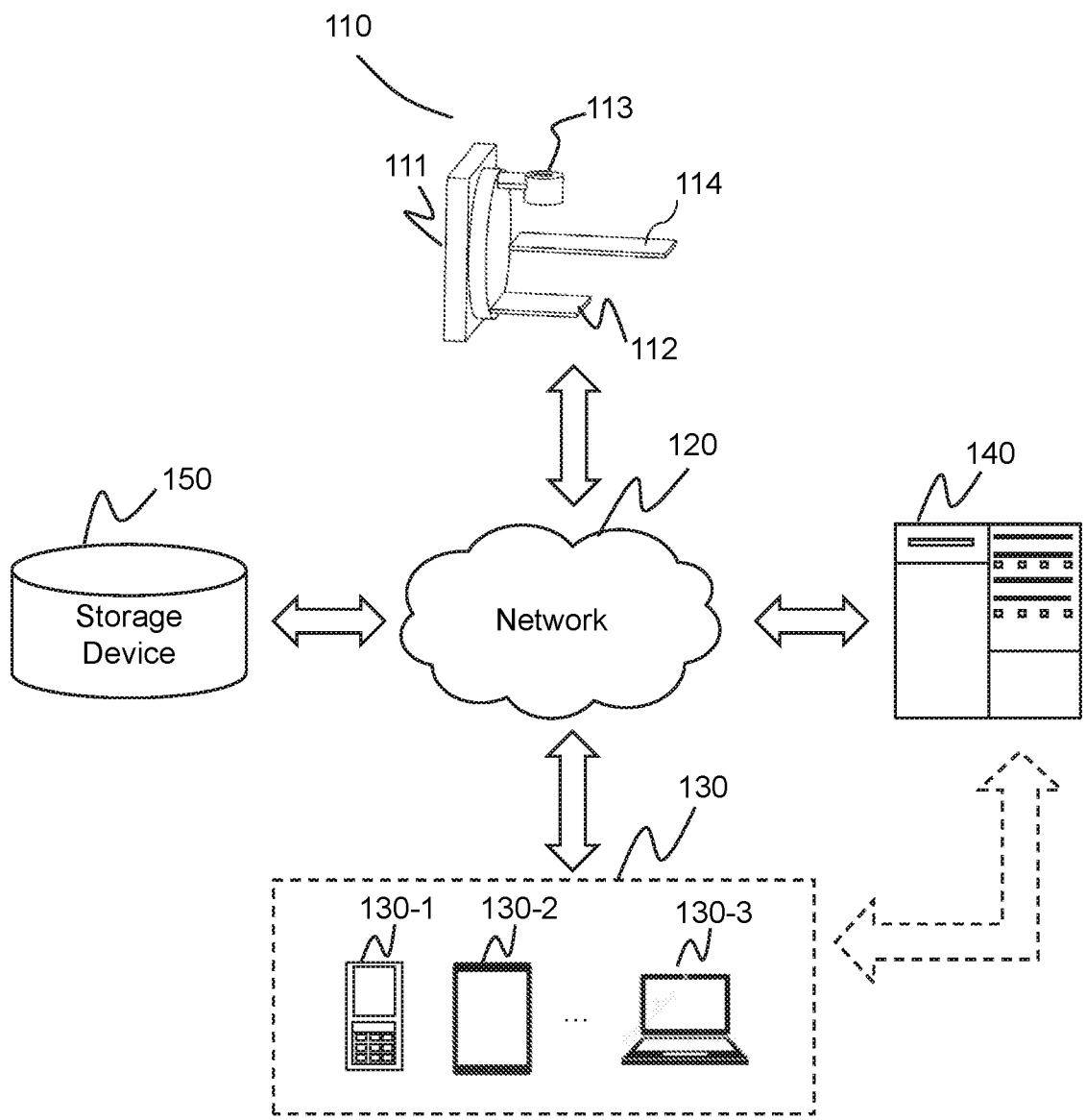
FIGS. 1A and 1B are schematic diagrams illustrating an exemplary medical system according to some embodiments of the present disclosure.
Figure 1B:
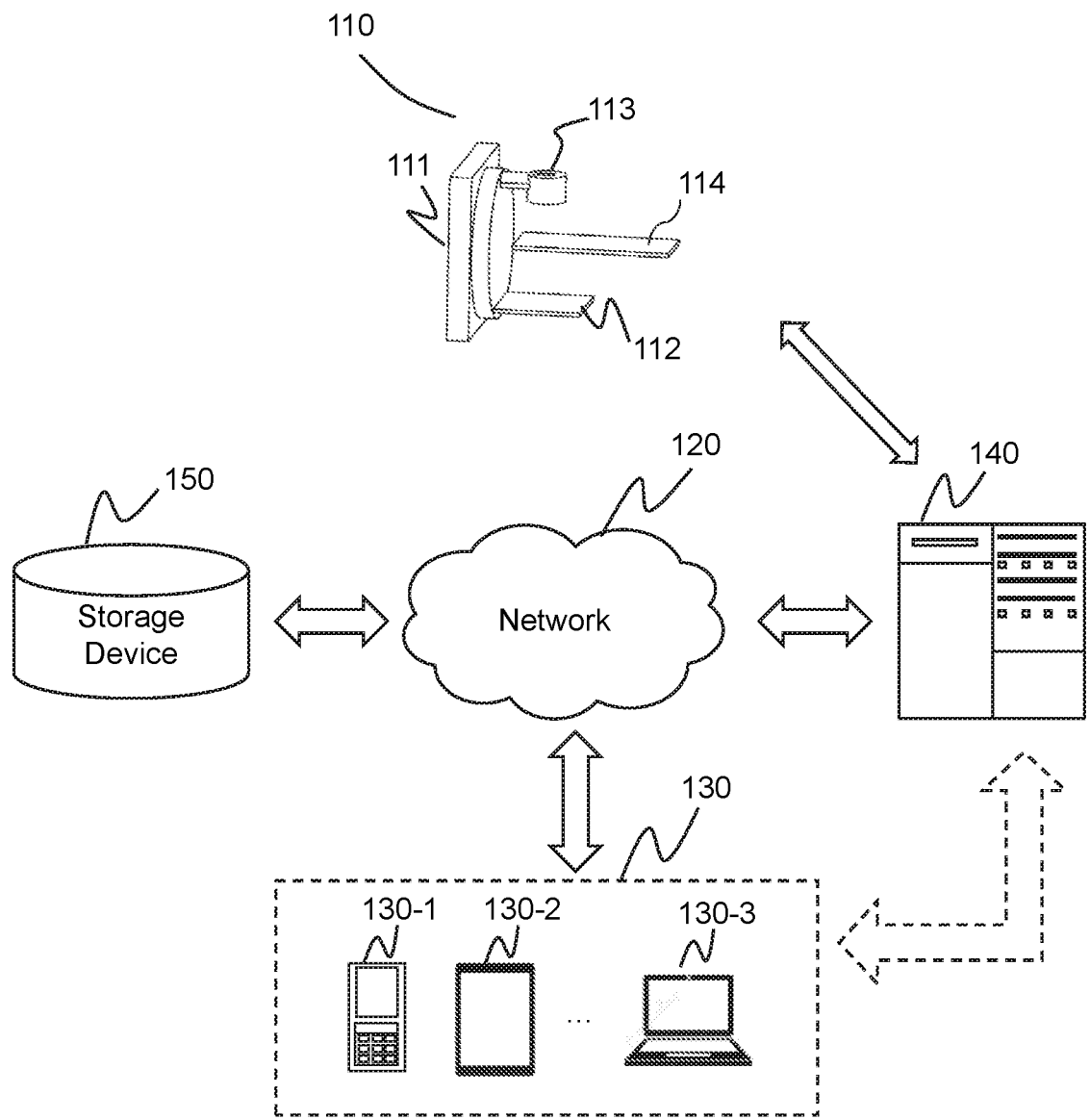

FIGS. 1A and 1B are schematic diagrams illustrating an exemplary medical system 100 according to some embodiments of the present disclosure. The medical system 100 may include a radiation device 110, a network 120, a terminal 130, a processing device 140, and a storage device 150. The connection between the components in the medical system 100 may be variable. Merely by way of example, as illustrated in FIG. 1A, the radiation device 110 may be connected to the processing device 140 through the network 120. As another example, as illustrated in FIG. 1B, the radiation device 110 may be connected to the processing device 140 directly.

The radiation device 110 may include a gantry 111, a detector 112, a radiation source 113, and a subject table 114. The gantry 111 may support the detector 112, the radiation source 113, etc. A subject to be scanned may be placed on the subject table 114. The radiation source 113 may emit radiation rays to the subject. In some embodiments, the radiation source 113 may emit rays with suitable energy (e.g. greater than 160 keV) for treatment. In some embodiments, the radiation source 113 may emit rays with suitable energy (e.g., generally less than 160 keV) for imaging. The detector 112 may detect radiation (e.g., X-ray photons) emitted from the radiation source 113. In some embodiments, the detector 112 may include a plurality of detector units. The detector units may include a scintillation detector (e.g., a detector consisting of GOS, cesium iodide) or a gas detector. The detector unit may be a flat panel detector. The detector unit may be a single-row detector or a multi-rows detector.

In some embodiments, the radiation device 110 may include an IGRT (image guided radio therapy) device. The IGRT device may use planning segmented images for accurately positioning the subject (e.g., organ).

The network 120 may facilitate exchange of information and/or data. In some embodiments, one or more components in the medical system 100 (e.g., the radiation device 110, the terminal 130, the processing device 140, or the storage device 150) may send information and/or data to another component in the medical system 100 via the network 120. For example, the processing device 140 may obtain image data from the radiation device 110 via the network 120. As another example, the processing device 140 may obtain user instructions from the terminal 130 via the network 120. In some embodiments, the network 120 may be any type of wired or wireless network, or combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof. In some embodiments, the network 120 may include one or more network access points. For example, the network 120 may include wired or wireless network access points such as base stations and/or internet exchange points through which one or more components of the medical system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, a smart footgear, smart glass, a smart helmet, a smart watch, smart clothing, a smart backpack, a smart accessory, or the like, or any combination thereof. In some embodiments, the smart mobile device may include a smartphone, a personal digital assistance (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a Hololens, a Gear VR, etc. In some embodiments, the terminal 130 may be part of the processing device 140. In some embodiments, the terminal 130 may be omitted.

The processing device 140 may process data and/or information obtained from the radiation device 110, the terminal 130, or the storage device 150. For example, the processing device 140 may process image data and determine a regularization item that may be used to modify the image data. In some embodiments, the processing device 140 may be a single server or a server group. The server group may be centralized or distributed. In some embodiments, the processing device 140 may be local or remote. For example, the processing device 140 may access information and/or data stored in the radiation device 110, the terminal 130, and/or the storage device 150 via the network 120. As another example, the processing device 140 may be directly connected to the radiation device 110, the terminal 130 and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 200 having one or more components illustrated in FIG. 2 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components in the medical system 100 (e.g., the processing device 140, the terminal 130). One or more components of the medical system 100 may access the data or instructions stored in the storage device 150 via the network 120. In some embodiments, the storage device 150 may be directly connected to or communicate with one or more components in the medical system 100 (e.g., the processing device 140, the terminal 130). In some embodiments, the storage device 150 may be part of the processing device 140.

FIG. 2 is a schematic diagram illustrating exemplary hardware and/or software components of an exemplary computing device 200 on which the processing device 140 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (program code) and perform functions of the processing device 140 in accordance with techniques described herein. The computer instructions may include routines, programs, objects, components, data structures, procedures, modules, and functions, which perform particular functions described herein. For example, the processor 210 may process image data obtained from the radiation device 110, the terminal 130, the storage device 150, or any other component of the medical system 100. In some embodiments, the processor 210 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field-programmable gate array (FPGA), an advanced RISC system (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both step A and step B, it should be understood that step A and step B may also be performed by two different processors jointly or separately in the computing device 200 (e.g., a first processor executes step A and a second processor executes step B, or the first and second processors jointly execute steps A and B).

The storage 220 may store data/information obtained from the radiation device 110, the terminal 130, the storage device 150, or any other component of the medical system 100. In some embodiments, the storage 220 may include a mass storage, removable storage, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 140 for determining a regularization item.

The I/O 230 may input or output signals, data, or information. In some embodiments, the I/O 230 may enable a user interaction with the processing device 140. In some embodiments, the I/O 230 may include an input device and an output device. Exemplary input device may include a keyboard, a mouse, a touch screen, a microphone, or the like, or a combination thereof. Exemplary output device may include a display device, a loudspeaker, a printer, a projector, or the like, or a combination thereof. Exemplary display device may include a liquid crystal display (LCD), a light-emitting diode (LED)-based display, a flat panel display, a curved screen, a television device, a cathode ray tube (CRT), or the like, or a combination thereof.

The communication port 240 may be connected to a network (e.g., the network 120) to facilitate data communications. The communication port 240 may establish connections between the processing device 140 and the radiation device 110, the terminal 130, or the storage device 150. The connection may be a wired connection, a wireless connection, or combination of both that enables data transmission and reception. The wired connection may include an electrical cable, optical cable, telephone wire, or the like, or any combination thereof. The wireless connection may include Bluetooth, Wi-Fi, WiMax, WLAN, ZigBee, mobile network (e.g., 3G, 4G, 5G), or the like, or a combination thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
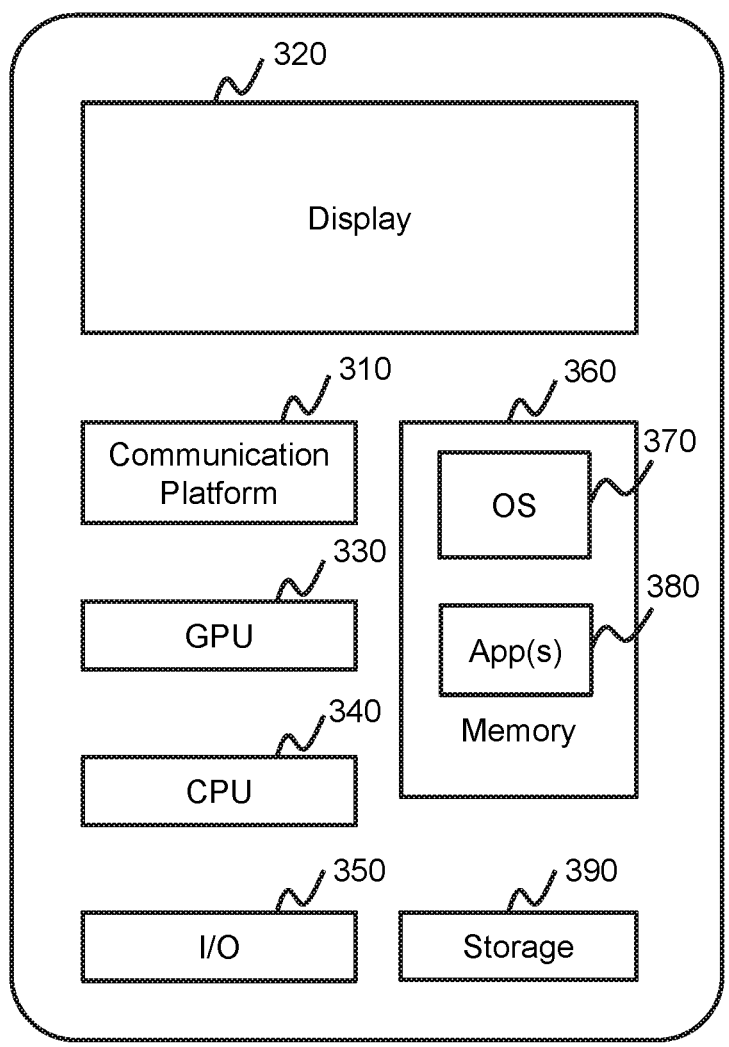
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS, Android, Windows Phone) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the medical system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

Figure 4:
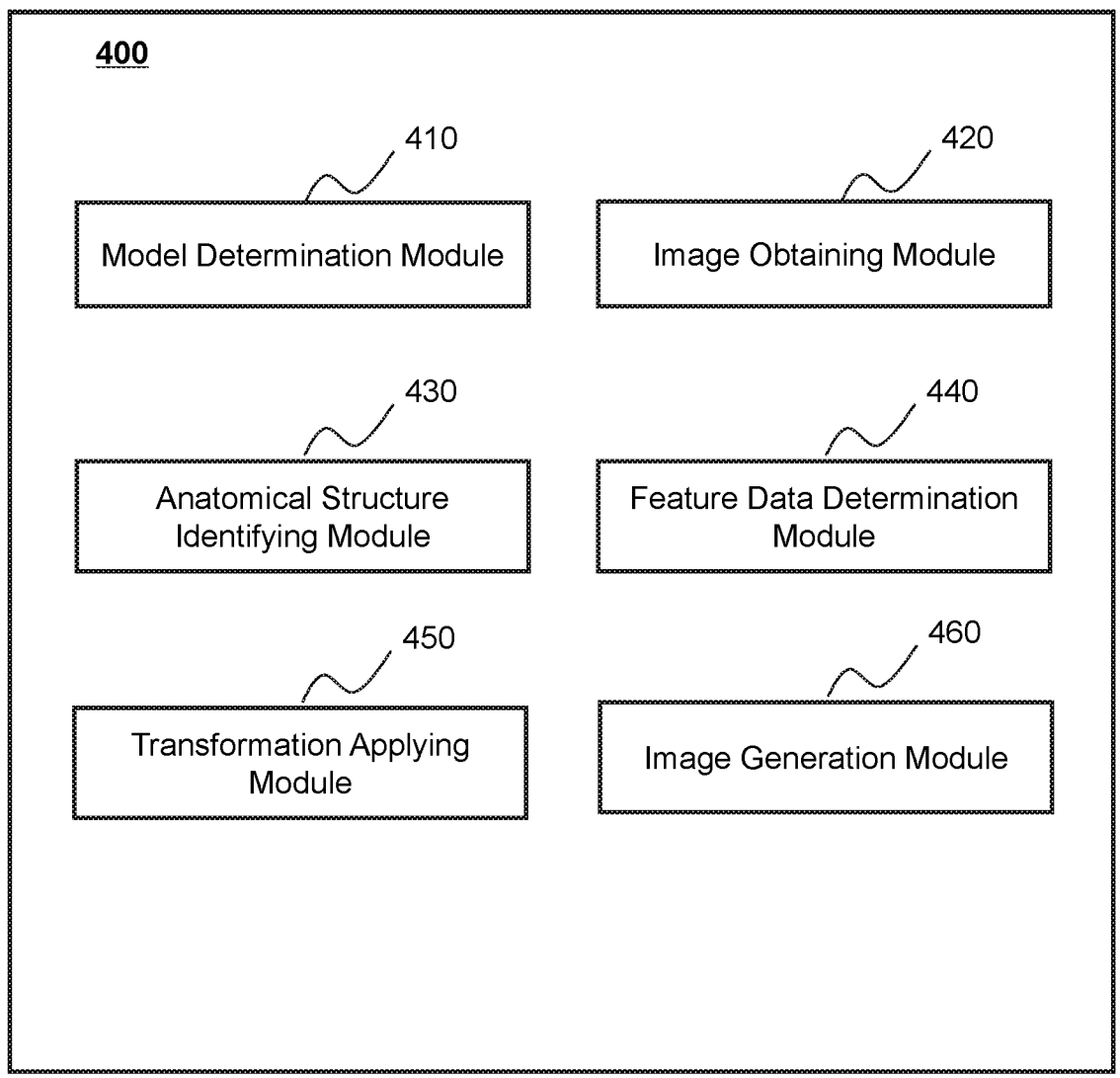
FIG. 4 is a schematic diagram illustrating an exemplary processor according to some embodiments of the present disclosure.

FIG. 4 is a schematic diagram illustrating an exemplary processing device 140 according to some embodiments of the present disclosure. The processing device 140 may be implemented on the computing device 200 (e.g., the processor 210) illustrated in FIG. 2. The processing device 140 may include a model determination module 410, an image obtaining module 420, an anatomical structure identifying module 430, a feature data determination module 440, a transformation applying module 450, and an image generation module 460.

The model determination module 410 may be configured to determine a segmentation model. The segmentation model may be used to segment an image that is input into the segmentation model. In some embodiments, the model determination module 410 may determine the segmentation model by training an initial segmentation model based on an augmented segmented image set of anatomical structure of an object (e.g., human).

The image obtaining module 420 may be configured to obtain an image of an object including one or more anatomical structures. Exemplary images of the organ may include MRI images (e.g., 2D MRI, 3D MRI, 2D streaming MRI, 4D volumetric MRI, 4D cine MRI), computed tomography (CT) images, cone-beam CT images, positron emission tomography (PET) images, functional MRI images (e.g., fMRI, DCE-MRI, diffusion MRI), X-ray images; fluoroscopic images, ultrasound images, radiotherapy portal images, single-photon emission computed tomography (SPECT) images, or the like, or any combination thereof. Exemplary organs may include head, heart, chest, breast, stomach, or the like, or any combination thereof.

In some embodiments, the image obtaining module 420 may obtain a treatment image containing the first anatomical structure (e.g., a tumor) of an object. In some embodiments, a treatment image may be a planning image for generating a radiation treatment planning. In some embodiments, a treatment image may be an image obtained during the treatment procedure, i.e., before a radiation therapy or during the radiation therapy. In some embodiments, the treatment image may be obtained after the radiation therapy. In some embodiments, the treatment image may be obtained after the treatment planning phase.

The anatomical structure identifying module 430 may identify a plurality of pixels with respect to an anatomical structure of the first object in the treatment image based on the segmentation model. The anatomical structure identifying module 430 may determine a plurality of pixels identifying the anatomical structure in the treatment image. In some embodiments, the anatomical structure identifying module 430 may identify a plurality of pixels with respect to the first anatomical structure of the first object in the treatment image based on the segmentation model. The anatomical structure identifying module 430 may determine the pixel values and the pixel locations of a plurality of pixels identifying the first anatomical structure in the treatment image. A pixel value may refer to the value of a property of a pixel. For instance, a pixel value may refer to the luminance value of a pixel, the grey value of a pixel, the color or RGB value of a pixel, the saturation value of a pixel, or the like, or a combination thereof.

The feature data determination module 440 may be configured to determine feature data of an anatomical structure in a first image. A first image may include a plurality of pixels identifying the anatomical structure e.g., (a first anatomical structure in the first image). The first image may include segmented information (e.g., a contour of the anatomical structure or an area of the anatomical structure, etc.) related to the anatomical structure. In some embodiments the first image may be an actual medical image. For example, the first image may be a planning image (e.g., a CT image) of a patient used for determining a treatment plan of radiation therapy. The treatment plan (e.g., a dose level of the treatment plan) may be determined based on the segmented information of the first image. The feature data of the anatomical structure may include the pixel values, the pixel locations of the plurality of pixels identifying the anatomical structure, a contrast noise ratio (CNR) with respect to the anatomical structure, or a CNR with respect to the image, a signal noise ratio (SNR) with respect to the anatomical structure, or a SNR with respect to the image, etc. In some embodiments, the feature data may include pixel values and pixel locations of a plurality of pixels representing a contour of the anatomical structure. In some embodiments, the feature data may include pixel values and pixel locations of a plurality of pixels representing an inner area encompassed by the contour of the anatomical structure. In some embodiments, contrast and noise may be two parameters for determining image quality. The CNR may be used to evaluate a degradation of the contrast and an estimate of the noise in the image. In some embodiments, the CNR may be defined as a ratio of a difference of signal intensities of two local regions of an image to background noise of the image. In some embodiments, the smaller the CNR is, the better the image quality may be. In some embodiments, the CNR may be related with a radiation dose, a tube voltage, a cathode-anode current, or the like, or any combination thereof. In some embodiments, a signal noise ratio (SNR) may be used as a parameter for determining image quality. The SNR may be used to evaluate a degradation of the contrast and an estimate of the noise in the image. In some embodiments, the SNR may be defined as a ratio of a difference of signal intensities of two local regions of an image to background noise of the image. In some embodiments, the smaller the SNR is, the better the image quality may be. In some embodiments, the SNR may be related with a radiation dose, a tube voltage, a cathode-anode current, or the like, or any combination thereof.

The transformation applying module 450 may determine one or more transformation related to an anatomical structure. A transformation may include a transformation type and one or more transformation parameters related to the transformation type. The transformation may refer to changing the pixel values and the pixel locations of the plurality of pixels identifying the anatomical structure in an image based on the transformation type and the one or more transformation parameters. In some embodiments, the transformation applying module 450 may determine the one or more transformation parameters related to the transformation type based on one or more parameter constraints. The transformation type may include a displacement of an anatomical structure, a rotation of the anatomical structure, a deformation of the anatomical structure, an appearance of an extra structure of the anatomical structure, a disappearance of a partial of the anatomical structure, and a contrast noise ratio (CNR). In some embodiments, contrast and noise may be two parameters for determining image quality. The CNR may be used to evaluate a degradation of the contrast and an estimate of the noise in the image. In some embodiments, the CNR may be defined as a ratio of a difference of signal intensities of two local regions of an image to background noise of the image. In some embodiments, the smaller the CNR is, the better the image quality may be. In some embodiments, the CNR may be related with a radiation dose, a tube voltage, a cathode-anode current, or the like, or any combination thereof.

The transformation applying module 450 may apply one or more transformations to first feature data of the anatomical structure to generate second feature data of the anatomical structure. First feature data may refer to feature data of an original anatomical structure included in an image obtained by the image obtaining module 420 and second feature data may refer to feature data of a transformed anatomical structure based on the one or more transformations. For instance, the feature data of a first anatomical structure in the first image may be the first feature data. The second feature data may be generated by applying the one or more transformations to first feature data.

The image generation module 460 may be configured to generate a training image based on the second feature data of the anatomical structure. In some embodiments, the image generation module 460 may generate one or more training images based on different transformations with different transformation types and different transformation parameters. The image generation module 460 may generate the augmented segmented image set based on the one or more training images.

It should be noted that the above description of the processing device 140 is provided for the purpose of illustration, and is not intended to limit the scope of the present disclosure. For persons having ordinary skills in the art, multiple variations and modifications may be made under the teaching of the present disclosure. However, those variations and modifications do not depart from the scope of the present disclosure.

Figure 5:
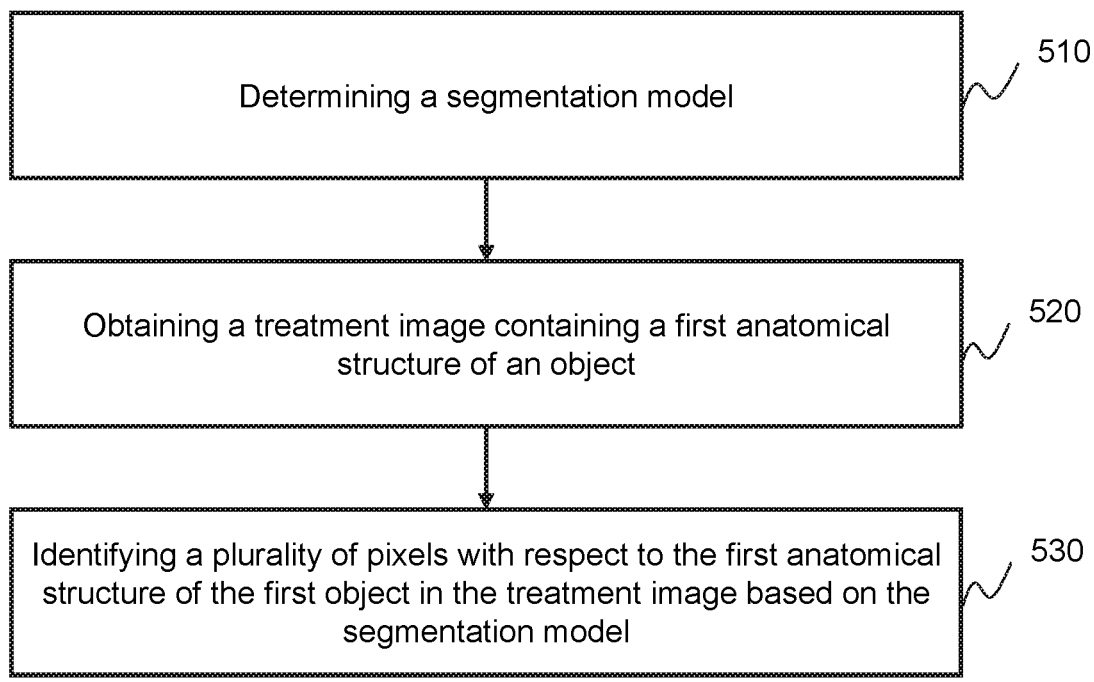
FIG. 5 is a flowchart illustrating an exemplary process for anatomical structure segmentation of an image according to some embodiments of the present disclosure.

FIG. 5 is a flowchart illustrating an exemplary process 500 for anatomical structure segmentation of an image according to some embodiments of the present disclosure.

The process 500 may be executed by the medical system 100. For example, the process 500 may be implemented as a set of instructions (e.g., an application) stored in the storage 220. The processing device 140 may execute the set of instructions and may accordingly be directed to perform the process 500. The operations of the illustrated process 500 presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described herein is not intended to be limiting.

In 510, the model determination module 410 may determine a segmentation model. The segmentation model may be used to identify a plurality of pixels representing a first anatomical structure included in an image that is input into the segmentation model. Exemplary images may include MRI images (e.g., 2D MRI, 3D MRI, 2D streaming MRI, 4D volumetric MRI, 4D cine MRI), computed tomography (CT) images, cone-beam CT images, positron emission tomography (PET) images, functional MRI images (e.g., fMRI, DCE-MRI, diffusion MRI), X-ray images; fluoroscopic images, ultrasound images, radiotherapy portal images, single-photon emission computed tomography (SPECT) images, or the like, or any combination thereof. The term "anatomical structure" in the present disclosure may refer to gas in the object (e.g., air), liquid in the object (e.g., water), solid in the object (e.g., stone), cell of the object, tissue of the object (e.g., tumor tissue), organ of the object (e.g., head, heart, chest, breast, stomach, etc.), or any combination thereof, which displayed in medical image (e.g., the first image, etc.), or really existing in or on the object's body.

In some embodiments, the model determination module 410 may obtain an initial segmentation model and determine the segmentation model by training the initial segmentation model. The initial segmentation model may be generated based on a machine learning model. The machine learning model may include a convolutional neural network, an adaptive boosting model, a gradient boosting decision tree model, or the like, or any combination thereof.

For example, the initial segmentation model may be a convolutional neural network (CNN). In some embodiments, the CNN may include one or more input layers, one or more convolution layers, one or more pooling layers, one or more fully-connected layers and one or more output layer.

In some embodiments, the input layer may receive the image of the first anatomical structure. The convolution layers may then convolve the image of the first anatomical structure with multiple kernels using trainable weights. In some embodiments, the kernel may activate feature data of the first anatomical structure (e.g., a contour of the first anatomical structure). The kernel may activate different first anatomical structure features (e.g., different portions of the contour of the first anatomical structure) with different trainable weights. The pooling layer may reduce the size of the image of the first anatomical structure that is convoluted by the convolution layer and further extract the different first anatomical structure features activated by the kernel. In some embodiments, the convolution layer and the pooling layer may compose the feature extraction part of the CNN. Then, the fully-connected layer may weight and combine the extracted different first anatomical structure features to generate feature data of the first anatomical structure. Further, the output layer may output the feature data of the first anatomical structure. The model determination module 410 may identify the plurality of pixels representing the first anatomical structure based on the feature data of the first anatomical structure.

The input of the CNN may be an augmented segmented image set including one or more second images generated based on a first image. The second image may be an artificial image generated based on the first image, and may be used a sample to train the initial segmentation model. The first image may refer to an image containing a plurality of pixels representing an anatomical structure (e.g., a tumor). In some embodiments, the plurality of pixels representing a first anatomical structure has been pre-identified manually or automatically. The second image may include feature data of the first anatomical structure (e.g., second feature data of the first anatomical structure illustrated in FIG. 6A, FIG. 6B, and FIG. 6C.) Then the model determination module 410 may generate an error function based on the difference between the feature data of the first anatomical structure feature outputted by the output layer and the predetermined feature data of the first anatomical structure in the second image (e.g., second feature data of the first anatomical structure illustrated in FIG. 6A, FIG. 6B, and FIG. 6C.) The model determination module 410 may input the error function back to the convolution layers and update the trainable weights of the kernel. The iterative procedure converges until the error function reaches a minimum value.

In some embodiments, the one or more second images may be generated by applying one or more transformations to the first anatomical structure in the first image. Detailed description of generating a second image may be found elsewhere in the present disclosure (e.g., in connection with FIG. 6A).

In 520, the image obtaining module 420 may obtain a treatment image containing the first anatomical structure (e.g., a tumor) of an object. A treatment image may be an actual image obtained during the treatment procedure, i.e., before a radiation therapy or during the radiation therapy. A treatment procedure may include a plurality of radiation therapies separated by a number of time periods. As the object may lose or gain weight during the treatment procedure, or the position of the object may be slightly different at different radiation therapy stages, the shape and/or position of the first anatomical structure may change during the treatment procedure.

In 530, the anatomical structure identifying module 430 may identify a plurality of pixels with respect to the first anatomical structure of the first object in the treatment image based on the segmentation model. The anatomical structure identifying module 430 may determine the pixel values and the pixel locations of a plurality of pixels identifying the first anatomical structure in the treatment image. A pixel value may refer to the value of a property of a pixel. For instance, a pixel value may refer to the luminance value of a pixel, the grey value of a pixel, the color or RGB value of a pixel, the saturation value of a pixel, or the like, or a combination thereof. In some embodiments, the anatomical structure identifying module 430 may segment the treatment image and generate segment information (e.g., a contour or an area of the first anatomical structure in the treatment image) based on the segmentation model. The treatment plan may be modified based on the treatment image with segment information.

It should be noted that the above description of the process 500 for determining the organ information of the organ of the patient in the image is provided for the purpose of illustration, and is not intended to limit the scope of the present disclosure. For persons having ordinary skills in the art, multiple variations and modifications may be made under the teaching of the present disclosure. However, those variations and modifications do not depart from the scope of the present disclosure. In some embodiments, the process 500 may also include other steps.

Figure 6A:
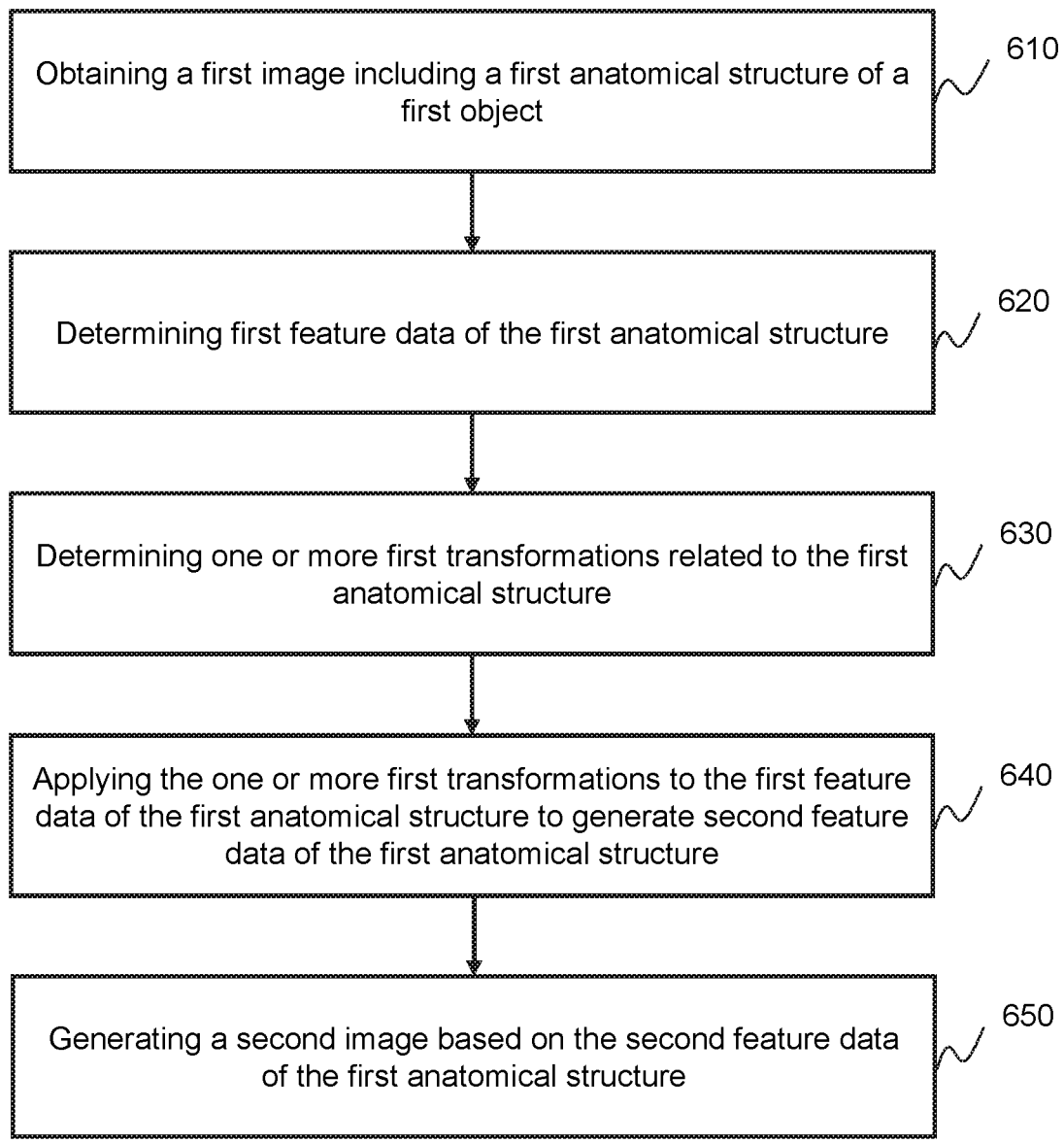
FIG. 6A is a flowchart illustrating an exemplary process for generating a second image according to some embodiments of the present disclosure.
Figure 6B:
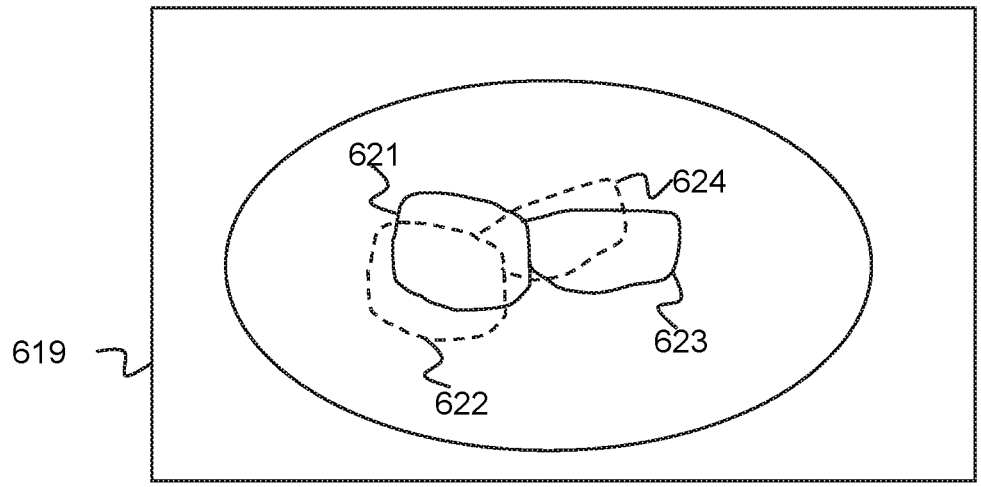
FIG. 6B and FIG. 6C are schematic diagrams illustrating generating a second image according to some embodiments of the present disclosure.
Figure 6C:
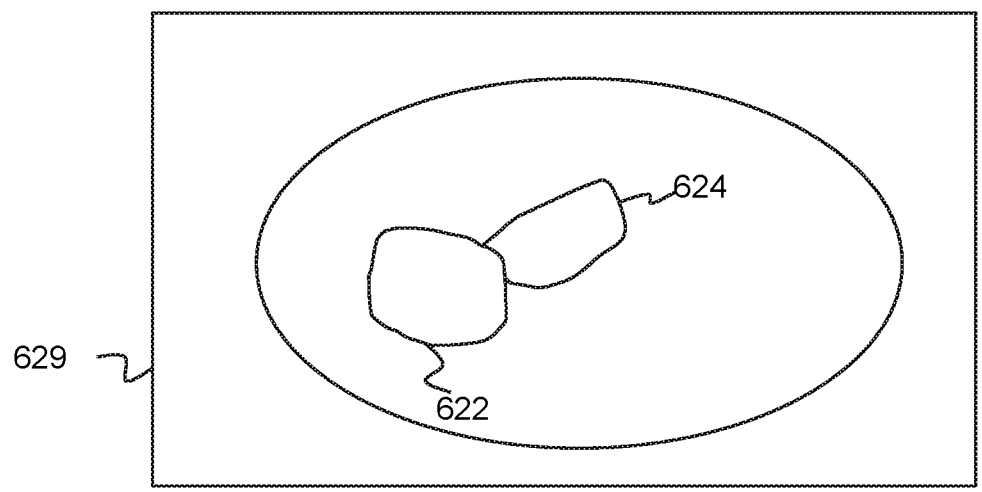

FIG. 6A is a flowchart illustrating an exemplary process 600 for generating a second image according to some embodiments of the present disclosure. FIG. 6B and FIG. 6C are diagrams illustrate generating the second image according to some embodiments of the present disclosure. The process 600 may be executed by the medical system 100. For example, the process 600 may be implemented as a set of instructions (e.g., an application) stored in the storage 220. The processing device 140 may execute the set of instructions and may accordingly be directed to perform the process 600. The operations of the illustrated process 600 presented below are intended to be illustrative. In some embodiments, the process 600 may be accomplished with one or more additional operations not described, and/or without one or more of the operations discussed. Additionally, the order in which the operations of the process 600 as illustrated in FIG. 6A and described herein is not intended to be limiting.

In 610, the image obtaining module 420 may obtain a first image including a first anatomical structure of a first object. In some embodiments, an object may be a mammal (e.g., orangutan, human, etc.) The term "anatomical structure" in the present disclosure may refer to gas in the object (e.g., air), liquid in the object (e.g., water), solid in the object (e.g., stone), cell of the object, tissue of the object (e.g., tumor tissue), organ of the object (e.g., head, heart, chest, breast, stomach, etc.), or any combination thereof, which displayed in an image (e.g., the first image, etc.), or really existing in or on the object's body.

The first image may include MRI images (e.g., 2D MRI, 3D MRI, 2D streaming MRI, 4D volumetric MRI, 4D cine MRI), computed tomography (CT) images, cone-beam CT images, positron emission tomography (PET) images, functional MRI images (e.g., fMRI, DCE-MRI, diffusion MRI), X-ray images; fluoroscopic images, ultrasound images, radiotherapy portal images, single-photon emission computed tomography (SPECT) images, or the like, or any combination thereof.

In 620, the feature data determination module 440 may determine first feature data of the first anatomical structure. The first image may include a plurality of pixels identifying the first anatomical structure. The first feature data of the first anatomical structure may include the pixel values and the pixel locations of the plurality of pixels identifying the first anatomical structure. In some embodiments, the first feature data may include pixel values and pixel locations of a plurality of first pixels representing a contour of the first anatomical structure. In some embodiments, the first feature data may include pixel values and pixel locations of a plurality of second pixels representing an inner area encompassed by the contour of the first anatomical structure. A pixel value may refer to the value of a property of the pixel. For instance, a pixel value may refer to the luminance value of a pixel, the grey value of a pixel, the color or RGB value of a pixel, the saturation value of a pixel, or the like, or a combination thereof.

In 630, the transformation applying module 450 may determine one or more first transformations related to the first anatomical structure. The one or more first transformations may refer to one or more transformations applied on the first anatomical structure. A transformation may include a transformation type and one or more transformation parameters related to the transformation type. The transformation may refer to changing the pixel values and the pixel locations of the plurality of pixels identifying an anatomical structure in an image based on the transformation type and the one or more transformation parameters. In some embodiments, the transformation applying module 450 may determine the one or more transformation parameters related to the transformation type based on one or more parameter constraints. For example, a transformation parameter related to a certain transformation type may have to be within a constraint range or may not exceed a constraint threshold.

The transformation type may include a displacement of an anatomical structure, a rotation of the anatomical structure, a deformation of the anatomical structure, an appearance of an extra structure of the anatomical structure, a disappearance of a partial of the anatomical structure, and an adjustment of a contrast noise ratio (CNR) of the anatomical structure or a CNR of the image. FIG. 8A to FIG. 8E are diagrams illustrating different transformations according to some embodiments of the present disclosure.

Figure 8A:
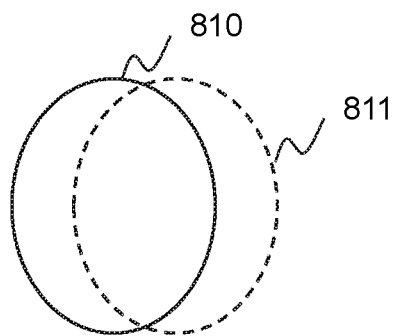

The displacement of the anatomical structure may refer to moving the plurality of pixels identifying the anatomical structure based on the one or more transformation parameters related to the displacement. The one or more transformation parameters related to the displacement of the anatomical structure may include a displacement distance and a displacement direction. As illustrated in FIG. 8A, according to a displacement of an anatomical structure, a plurality of pixels identifying an original anatomical structure 810 may be moved by a displacement vector to generate the plurality of pixels identifying a transformed anatomical structure 811. The displacement vector may be determined based on the displacement distance and the displacement direction. The parameter constraint of the displacement of the anatomical structure may be related to a constraint condition of the displacement of the anatomical structure. For instance, if the anatomical structure is a heart, the displacement parameters, i.e., the displacement distance and/or direction may be configured such that the plurality of pixels representing the heart are not displaced out of the thoracic cavity.

Figure 8B:
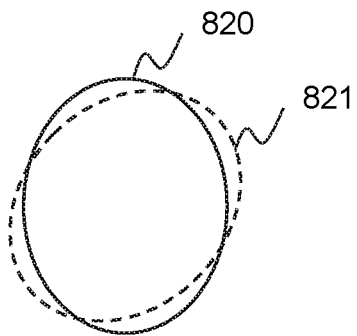

The rotation of the anatomical structure may refer to rotating the plurality of pixels identifying the anatomical structure by a certain angle. The transformation parameter related to the rotation of the anatomical structure may include a rotation angle. For example, as illustrated in FIG. 8B, according to the rotation of the anatomical structure, a plurality of pixels identifying an original anatomical structure 820 may be rotated by a rotation angle to generate the plurality of pixels identifying a transformed anatomical structure 821. The parameter constraint of the rotation of the anatomical structure may be related to a limit on the rotation angle of the anatomical structure. For instance, the rotation angle may not exceed 30 degrees.

Figure 8C:
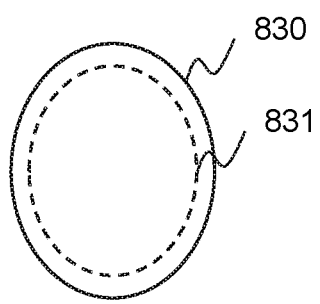

The deformation of the anatomical structure may refer to expanding or contracting the contour of the anatomical structure by changing locations of the plurality of first pixels representing the contour of the anatomical structure based on the one or more transformation parameters related to the deformation. The one or more transformation parameters related to the deformation of the anatomical structure may include a deformation direction and a deformation scale. In some embodiments, a positive deformation direction may represent expanding the contour of the anatomical structure, and a negative deformation direction may represent contracting the contour of the anatomical. As illustrated in FIG. 8C, according to the deformation of the anatomical structure, a plurality of pixels identifying the contour of an original anatomical structure 830 may contract in a certain scale to generate the plurality of pixels identifying a transformed anatomical structure 831. The parameter constraint of the deformation of the anatomical structure may be related to compressibility of the anatomical structure. For instance, the deformation scale of a liver may be smaller than the deformation scale of a rectum with gas filling.

Figure 8D:
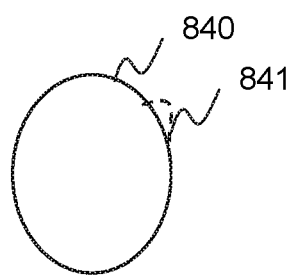

The appearance of the extra structure may refer to a new anatomical structure appearing on the original anatomical structure by changing pixel values of the plurality of pixels representing the original anatomical structure based on the one or more transformation parameters related to the appearance. For example, as illustrated in FIG. 8D, according to the appearance of an extra structure of an anatomical structure, a plurality of pixels identifying an extra structure 841 may be generated and attached to an original anatomical structure 840.

Figure 8E:
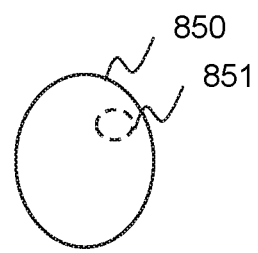

The disappearance of a partial of the anatomical structure may refer to that a portion of the anatomical structure may disappear by changing the pixel values of the plurality of pixels representing the anatomical structure based on the one or more transformation parameters related to the disappearance. For example, as illustrated in FIG. 8E, according to the disappearance of a partial of the anatomical structure, the pixel values of the plurality of pixels representing area 851 of an original anatomical structure 850 may be changed to show that the area 851 disappears.

Contrast and noise may be two parameters for determining image quality. The CNR may be used to evaluate a degradation of the contrast and an estimate of the noise in the image. In some embodiments, the CNR may be defined as a ratio of a difference of signal intensities of two local regions of an image to background noise of the image. In some embodiments, the smaller the CNR is, the better the image quality may be. In some embodiments, the CNR may be related with a radiation dose, a tube voltage, a cathode-anode current, or the like, or any combination thereof.

In 640, the transformation applying module 450 may apply the one or more first transformations to the first feature data of the first anatomical structure to generate second feature data of the first anatomical structure. The transformation applying module 450 may change the pixel values and the pixel locations of the plurality of pixels identifying the first anatomical structure to generate the second feature data of the first anatomical structure. In some embodiments, the transformation applying module 450 may change pixel values and pixel locations of a plurality of first pixels representing a contour of the first anatomical structure. In some embodiments, the transformation applying module 450 may change pixel values and the pixel locations of the plurality of second pixels representing an inner area encompassed by the contour of the first anatomical structure. For example, as shown in FIG. 6B, a first image 619 may include a first anatomical structure 621. The transformation applying module 450 may change pixel locations of a plurality of pixels representing contour of the first anatomical structure 621 to generate a new contour 622 of the first anatomical structure 621 as the second feature data of the first anatomical structure 621.

In some embodiments, the transformation applying module 450 may determine a reference frame by determining one or more fixed points in the first image, and determine the second feature data of the first anatomical structure based on the reference frame and the one or more transformation parameters. A fixed point in the first image may refer to one or more pixels representing an anatomical structure which would not move in a normal course of treatment (e.g., a bone). The transformation applying module 450 may change the pixel locations of the plurality of pixels identifying the first anatomical structure to generate the second feature data of the first anatomical structure with reference to the one or more fixed points. The one or more first transformations may refer to one or more transformations applied on the first anatomical structure. For example, the transformation applying module 450 may apply different transformations (e.g., a displacement and a rotation) on the first anatomical structure. In some embodiments, the transformation applying module 450 determine a transformation sequence related to the one or more first transformations. For example, the transformation applying module 450 may first apply the displacement on the first anatomical structure followed by the rotation on the first anatomical structure based on the transformation sequence.

In some embodiments, the transformation applying module 450 may apply an adjustment of the CNR to the first anatomical structure in the first image. For example, if the first anatomical structure in the first image is chest, the transformation applying module 450 may only apply an adjustment of the CNR to the chest. In some embodiments, the transformation applying module 450 may apply an adjustment of the CNR to the whole first image to match the CNR of the treatment image. In this way, a CNR of a second image generated based on the first image may be same as or similar with the CNR of the treatment image.

In 650, the image generation module 460 may generate a second image based on the second feature data of the first anatomical structure. For example, as illustrated in FIG. 6B and FIG. 6C, the image generation module 460 may generate a second image 629 based on the new contour 622 of the first anatomical structure 621 generated in operation 640.

In some embodiments, the image generation module 460 may generate one or more second images based on different transformations with different transformation types and different transformation parameters. The image generation module 460 may generate the augmented segmented image set based on the one or more second images.

It should be noted that the above description of the process 600 for generating a second image is provided for the purpose of illustration, and is not intended to limit the scope of the present disclosure. For persons having ordinary skills in the art, multiple variations and modifications may be made under the teaching of the present disclosure. However, those variations and modifications do not depart from the scope of the present disclosure. In some embodiments, the process 600 may also include other steps. For example, the first image may include a second anatomical structure of the first object. The transformation applying module 450 may apply one or more second transformations to first feature data of the second anatomical structure to generate second feature data of the second anatomical structure. The one or more second transformations may refer to one or more transformations applied on the second anatomical structure. The image generation module 460 may generate a second image based on the second feature data of the second anatomical structure. For example, as illustrated in FIG. 6B and FIG. 6C, the first image 619 may further include a second anatomical structure 623. The transformation applying module 450 may change pixel locations of a plurality of pixels representing contour of the second anatomical structure 623 to generate a new contour 624 of the second anatomical structure 623 as the second feature data of the second anatomical structure 623. In some embodiments, the transformation applying module 450 may determine a priority order between the first anatomical structure and the second anatomical structure. The image generation module 460 may generate the second image further based on the priority order. For example, the transformation applying module 450 may first apply the one or more first transformations to the first anatomical structure followed by the one or more second transformations to the second anatomical structure.

In some embodiments, the transformation applying module 450 may transform a CNR of a first image so that the CNR of the first image matches a CNR of the treatment image. In this way, a CNR of the second image generated based on the first image may be same as or similar with the CNR of the treatment image. For example, if the first image is a planning CT image generated at 120 Kv with a first CNR, and the treatment image is a treatment CT image generated at 6 Mv with a second CNR, the transformation applying module 450 may transform the first CNR to match the second CNR.

In some embodiments, the transformation applying module 450 may transform feature data of a first image obtained by a first modality (e.g., PET, MRI, CT, etc.) so that the feature data of the first image matches the feature data of the treatment image obtained by a second modality (e.g., PET, MRI, CT, etc.). For instance, if the first image is a planning PET image with a first CNR, and the treatment image is a treatment MR image with a second CNR, the transformation applying module 450 may transform the first CNR to match the second CNR. The transformation applying module 450 may then apply a transformation with respect to a shape of an anatomical structure in the first image to the first image with the transformed CNR.

Figure 7A:
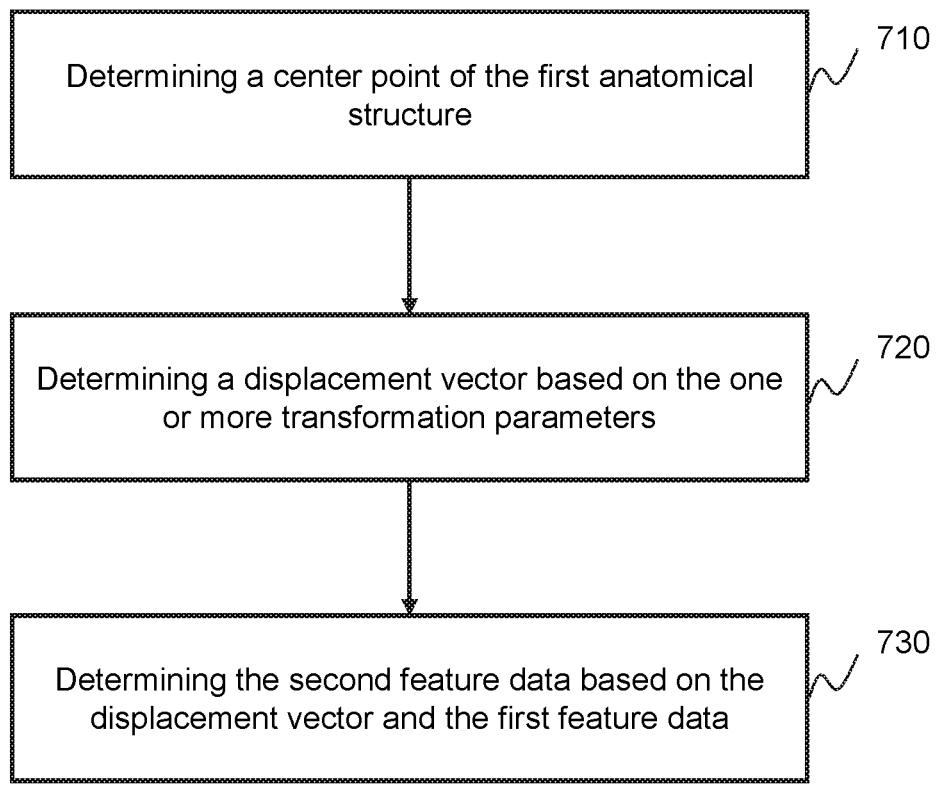
FIG. 7A is a flowchart illustrating an exemplary process for applying a transformation of displacement to the first feature data to generate second feature data of the first anatomical structure according to some embodiments of the present disclosure.
Figure 7B:
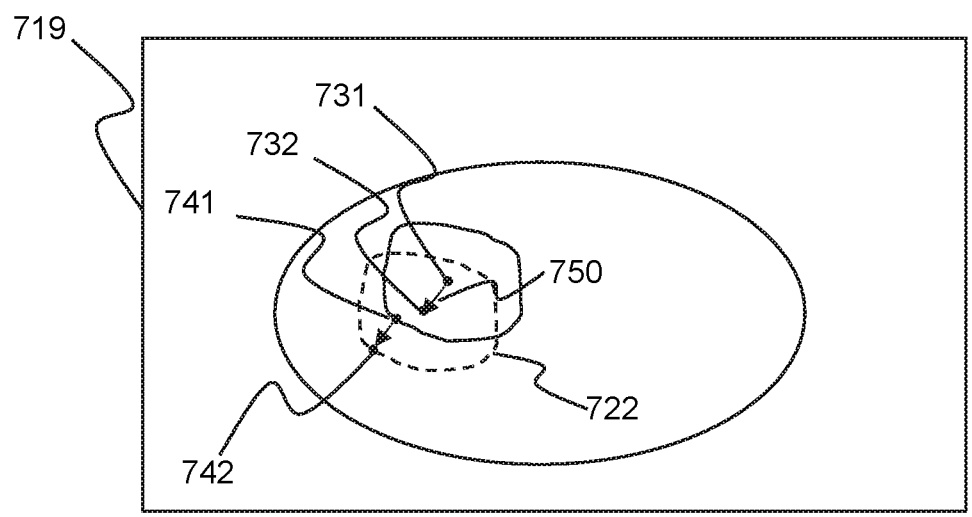
FIG. 7B is a diagram illustrating applying the transformation of displacement to the first feature data to generate second feature data of the first anatomical structure according to some embodiments of the present disclosure; and, FIGS. 8A to 8E are diagrams illustrating different transformations according to some embodiments of the present disclosure.

FIG. 7A is a flowchart illustrating an exemplary process 700 for applying a transformation of a displacement to the first feature data to generate second feature data of the first anatomical structure according to some embodiments of the present disclosure. FIG. 7B is a diagram illustrating applying the transformation of the displacement to the first feature data to generate second feature data of the first anatomical structure according to some embodiments of the present disclosure. The process 700 may be executed by the medical system 100. For example, the process 700 may be implemented as a set of instructions (e.g., an application) stored in the storage 220. The processing device 140 may execute the set of instructions and may accordingly be directed to perform the process 700. The operations of the illustrated process 700 presented below are intended to be illustrative. In some embodiments, the process 700 may be accomplished with one or more additional operations not described, and/or without one or more of the operations discussed. Additionally, the order in which the operations of the process 700 as illustrated in FIG. 7A and described herein is not intended to be limiting.

In 710, the feature data determination module 440 may determine a center point of the first anatomical structure. In some embodiments, the center point may be a mass center of an anatomical structure or a volume center of the anatomical structure. Taking FIG. 7B as an example, a first image 719 may include a first anatomical structure 721 represented by the first feature data of the first anatomical structure 721, and a first anatomical structure 722 represented by the second feature data of the first anatomical structure 722. Point 731 may be a center point of the first anatomical structure 721, and point 732 may be a center point of the first anatomical structure 722. A reference frame may be determined based on one or more fixed points in the first image. An original position of the first anatomical structure in the first image may be determined based on the center point of the first anatomical structure and the reference frame.

In 720, the transformation applying module 450 may determine a displacement vector based on the one or more transformation parameters. The one or more transformation parameters related to the displacement may include a direction of the displacement and a distance of the displacement. The transformation applying module 450 may determine a displacement vector based on the direction of the displacement and the distance of the displacement.

In 730, the transformation applying module 450 may determine the second feature data based on the displacement vector and the first feature data. In some embodiments, the transformation applying module 450 may determine the second feature data of the first anatomical structure based on the original position of the first anatomical structure and the one or more transformation parameters. As shown in FIG. 7B, the transformation applying module 450 may generate the first anatomical structure 722 based on the displacement vector and the first anatomical structure 721. A vector 750 from point 731 to point 732 may be the displacement vector. The transformation applying module 450 may move all the plurality of pixels identifying the first anatomical structure based on the displacement vector to generate the first anatomical structure 722. For example, the transformation applying module 450 may move a pixel located on point 741 (i.e., on the contour of the first anatomical structure 721) based on the displacement vector to point 742 (i.e., on the contour of the first anatomical structure 722).

It should be noted that the above description of the process 700 for applying a transformation to the first feature data to generate second feature data is provided for the purpose of illustration, and is not intended to limit the scope of the present disclosure. For persons having ordinary skills in the art, multiple variations and modifications may be made under the teaching of the present disclosure. However, those variations and modifications do not depart from the scope of the present disclosure. In some embodiments, the process 700 may also include other steps.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, system, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing device having at least one processor, and at least one computer-readable storage medium, the method comprising:
obtaining a segmentation model configured to identify a plurality of pixels representing an anatomical structure in an image, wherein the segmentation model is determined by training an initial model using one or more second images, and the one or more second images are artificial images generated based on one or more first images, each of the one or more second images is generated by a process including:
extracting a first anatomical structure from one of the one or more first images;
generating a transformed anatomical structure by transforming at least one of an area, a location, or a shape of a contour of the extracted first anatomical structure; and
generating the second images based on the transformed anatomical structure;
obtaining a treatment image relating to the anatomical structure; and
identifying a plurality of pixels representing the anatomical structure in the treatment image using the segmentation model.

2. The method of claim 1, wherein the identifying a plurality of pixels representing the anatomical structure in the treatment image includes:
identifying pixel values or pixel locations of the plurality of pixels.

3. The method of claim 1, further comprising:
determining segment information associated with the anatomical structure by segmenting, using the segmentation model, the treatment image.

4. The method of claim 3, wherein the segment information associated with the anatomical structure includes at least one of a contour of the anatomical structure or an area of the anatomical structure.

5. The method of claim 1, wherein the one or more second images are generated by the process comprising:
obtaining first feature data of the first anatomical structure in the one or more first images;
determining one or more transformations related to the first anatomical structure in the one or more first images;
generating second feature data related to the transformed anatomical structure by applying the one or more transformations to the first feature data; and
generating the one or more second images based on the second feature data.

6. The method of claim 5, wherein the one or more transformations include at least one of a transformation type or one or more transformation parameters related to the transformation type.

7. The method of claim 6, wherein the transformation type includes at least one of a displacement of the first anatomical structure, a rotation of the first anatomical structure, a deformation of the first anatomical structure, an appearance of an extra structure, or a disappearance of partial of the first anatomical structure.

8. The method of claim 7, wherein the one or more transformation parameters related to the transformation type include at least one of a displacement distance, a displacement direction, a rotation angle, a deformation direction, or a deformation scale.

9. The method of claim 5, wherein the segmentation model is determined by a process comprising:
for each of at least one of the one or more second images, inputting the second image into the initial model;
outputting feature data of the anatomical structure in the second image;
generating an error function based on a difference between the outputted feature data of the anatomical structure and the second feature data of the anatomical structure in the second image; and
updating one or more parameters of the initial model based on the error function; and
determining the segmentation model based on the one or more updated parameters.

10. The method of claim 9, wherein the one or more parameters include weights of kernels of the initial model.

11. The method of claim 1, wherein the segmentation model includes at least one of a convolutional neural network, an adaptive boosting model, or a gradient boosting decision tree model.

12. The method of claim 5, wherein the generating the second feature data related to the transformed anatomical structure by applying the one or more transformations to the first feature data includes:
  determining a reference frame by determining one or more fixed points in the first image; and
  determining the second feature data related to the transformed anatomical structure based on the reference frame and the one or more transformation parameters.

13. The method of claim 5, wherein the generating the second feature data related to the transformed anatomical structure by applying the one or more transformations to the first feature data includes:
  determining a center point of the first anatomical structure;
  determining a displacement vector based on the one or more transformation parameters; and
  determining the second feature data based on the displacement vector and the center point of the first anatomical structure.

14. The method of claim 1, wherein the segmentation model is determined by training the initial model using a combination of the one or more first images and the one or more second images.

15. A system comprising:
  a non-transitory storage medium storing a set of instructions;
  a processor in communication with the non-transitory storage medium, wherein when executing the set of instructions, the processor is directed to perform operations including:
    obtaining a segmentation model configured to identify a plurality of pixels representing an anatomical structure in an image, wherein the segmentation model is determined by training an initial model using one or more second images, and the one or more second images are artificial images generated based on one or more first images, each of the one or more second images is generated by a process including:
      extracting a first anatomical structure from one of the one or more first images;
      generating a transformed anatomical structure by transforming at least one of an area, a location, or a shape of a contour of the extracted first anatomical structure; and
      generating the second image based on the transformed anatomical structure;
    obtaining a treatment image relating to the anatomical structure; and
    identifying a plurality of pixels representing the anatomical structure in the treatment image using the segmentation model.

16. The system of claim 15, wherein to identify a plurality of pixels representing the anatomical structure in the treatment image, the processor is directed to perform the operations including:
  identifying pixel values or pixel locations of the plurality of pixels.

17. The system of claim 15, wherein the processor is directed further to perform the operations including:
  determining segment information associated with the anatomical structure by segmenting, using the segmentation model, the treatment image.

18. The system of claim 15, wherein the one or more second images are generated by the process comprising:
  obtaining first feature data of the first anatomical structure in the one or more first images;
  determining one or more transformations related to the first anatomical structure in the one or more first images;
  generating second feature data related to the transformed anatomical structure by applying the one or more transformations to the first feature data; and
  generating the one or more second images based on the second feature data.

19. The system of claim 18, wherein the segmentation model is determined by a process comprising:
  for each of at least one of the one or more second images,
    inputting the second image into the initial model;
    outputting feature data of the anatomical structure in the second image;
    generating an error function based on a difference between the outputted feature data of the anatomical structure and the second feature data of the anatomical structure in the second image;
    updating one or more parameters of the initial model based on the error function; and
  determining the segmentation model based on the one or more updated parameters.

20. A non-transitory computer readable medium, comprising:
  instructions being executed by at least one processor, causing the at least one processor to implement a method, the method comprising:
    obtaining a segmentation model configured to identify a plurality of pixels representing an anatomical structure in an image, wherein the segmentation model is determined by training an initial model using one or more second images, and the one or more second images are artificial images generated based on one or more first images, each of the one or more second images is generated by a process including:
      extracting a first anatomical structure from one of the one or more first images;
      generating a transformed anatomical structure by transforming at least one of an area, a location, or a shape of a contour of the extracted first anatomical structure; and
      generating the second images based on the transformed anatomical structure;
    obtaining a treatment image relating to the anatomical structure; and
    identifying a plurality of pixels representing the anatomical structure in the treatment image using the segmentation model.

* * * * *